US012661379B2

(12) United States Patent (10) Patent No.: US 12,661,379 B2
Kim et al. (45) Date of Patent: Jun. 23, 2026

(54) COMPOSITION COMPRISING CRICKET OR EXTRACT THEREOF FOR IMPROVING BOWEL MOVEMENT FUNCTION

(71) Applicant: CJ CHEILJEDANG CORPORATION, Jung-gu (KR)

(72) Inventors: Yeo Jin Kim, Suwon-si (KR); Su Jin Bae, Suwon-si (KR); Dong Joo Shin, Suwon-si (KR)

(73) Assignee: CJ CHEILJEDANG CORPORATION, Jung-gu (KR)

( * ) Notice: Subject to any disclaimer, the term of this patent is extended or adjusted under 35 U.S.C. 154(b) by 686 days.

(21) Appl. No.: 17/920,713

(22) PCT Filed: Apr. 23, 2021

(86) PCT No.: PCT/KR2021/005194
§ 371 (c)(1),
(2) Date: Oct. 21, 2022

(87) PCT Pub. No.: WO2021/215887
PCT Pub. Date: Oct. 28, 2021

(65) Prior Publication Data
US 2023/0165910 A1 Jun. 1, 2023

(30) Foreign Application Priority Data

Apr. 23, 2020 (KR) ........................ 10-2020-0049495

(51) Int. Cl.
*A61K 35/64* (2015.01)
*A61P 1/10* (2006.01)
*A61P 3/04* (2006.01)
(52) U.S. Cl.
CPC ................ *A61K 35/64* (2013.01); *A61P 1/10* (2018.01); *A61P 3/04* (2018.01)
(58) Field of Classification Search
None
See application file for complete search history.

(56) References Cited

U.S. PATENT DOCUMENTS

| | | | |
|---|---|---|---|
| 2017/0165195 A1 | 6/2017 | Lee | |
| 2019/0365827 A1 | 12/2019 | Lee | |
| 2019/0374459 A1 | 12/2019 | Lee | |

FOREIGN PATENT DOCUMENTS

| | | | |
|---|---|---|---|
| JP | 2017-105772 A | 6/2017 | |
| JP | 2019-210269 A | 12/2019 | |

| | | | |
|---|---|---|---|
| KR | 10-2003-0005516 A | 1/2003 | |
| KR | 10-2004-0018233 A | 3/2004 | |
| KR | 10-2016-0041138 A | 7/2008 | |
| KR | 10-0847889 B1 | 7/2008 | |
| KR | 10-1702851 B1 | 2/2017 | |
| KR | 10-1850308 B1 | 4/2018 | |
| KR | 10-1856602 B1 | 5/2018 | |
| KR | 10-1919839 B1 | 11/2018 | |
| KR | 10-2019-0003304 A | 1/2019 | |
| KR | 10-2026769 B1 | 3/2019 | |
| KR | 10-2019-0051876 A | 5/2019 | |

OTHER PUBLICATIONS

Jeong (KR 101919839 B1—English translation)—2018.*
Li (CN 102697876 A—English translation)—Oct. 3, 2012.*
Ruwa ("What to know about Crohn's disease and bowel movements" (https://perks.optum.com/blog/crohns-disease-poop—2023).*
Yun (KR 101790018 B1—English translation)—Oct. 25, 2017.*
Office Action issued on Sep. 5, 2024 for the corresponding Chinese Patent Application No. 202180029990.X (11 pages including English Translation).
Michelle Starr, "Eating crickets does something really good to your gut bacteria, study finds", Aug. 6, 2018, Science alert, Scientific Report, (3 pages).
Office Action issued on Sep. 11, 2023 for the corresponding Japanese patent application No. 2022-564452 (7 pages).
"Keichitsu—The number of people who eat insects is increasing in the world! What is the attraction of 'insects as food'? (Seasonal/living topics)", Usagida Risue, Japan Weather Association, Mar. 6, 2016, [Retrieved from internet on Sep. 5, 2023] URL: https://tenki.jp/suppl/usagida/2016/03/06/10681.html#sub-title-a (12 pages including machine translation).
International Search Report and Written Opinion of the International Searching Authority for International Patent Application No. PCT/KR2021/005194 mailed Aug. 5, 2021, 10 pages.
Notice of Allowance for Korean Patent Application No. 10-2020-0049495 mailed Jan. 20, 2022, 5 pages.
Finke, M., "Complete Nutrient Content of Four Species of Commercially Available Feeder Insects Fed Enhanced Diets During Growth", Zoo Biology, 34: 554-564 (2015).
"Kosoae Made with Edible Insect Mealworms", Naver blog, 19 pages (Sep. 29, 2017), retrieved from the Internet , "https://blog.naver.com/catives/221108161156".
Stull, V. et al., "Impact of Edible Cricket Consumption on Gut Microbiota in Healthy Adults, a Double-blind, Randomized Cross-over Trial", Scientific Reports, 8:10762, 1-13 (2018).
Sanyal et al., Phase 3 Trial of Semaglutide in Metabolic Dysfunction-Associated Steatohepatitis, The New England Journal of Medicine, vol. 392 No. 21 (Jun. 5, 2025); pp. 2089-2099.

* cited by examiner

*Primary Examiner* — Susan Hoffman
(74) *Attorney, Agent, or Firm* — Merchant & Gould P.C.

(57) ABSTRACT

The present invention relates to a composition comprising Cricket or an extract thereof for improving a bowel movement function or weight loss.

5 Claims, 2 Drawing Sheets

【Figure 1】
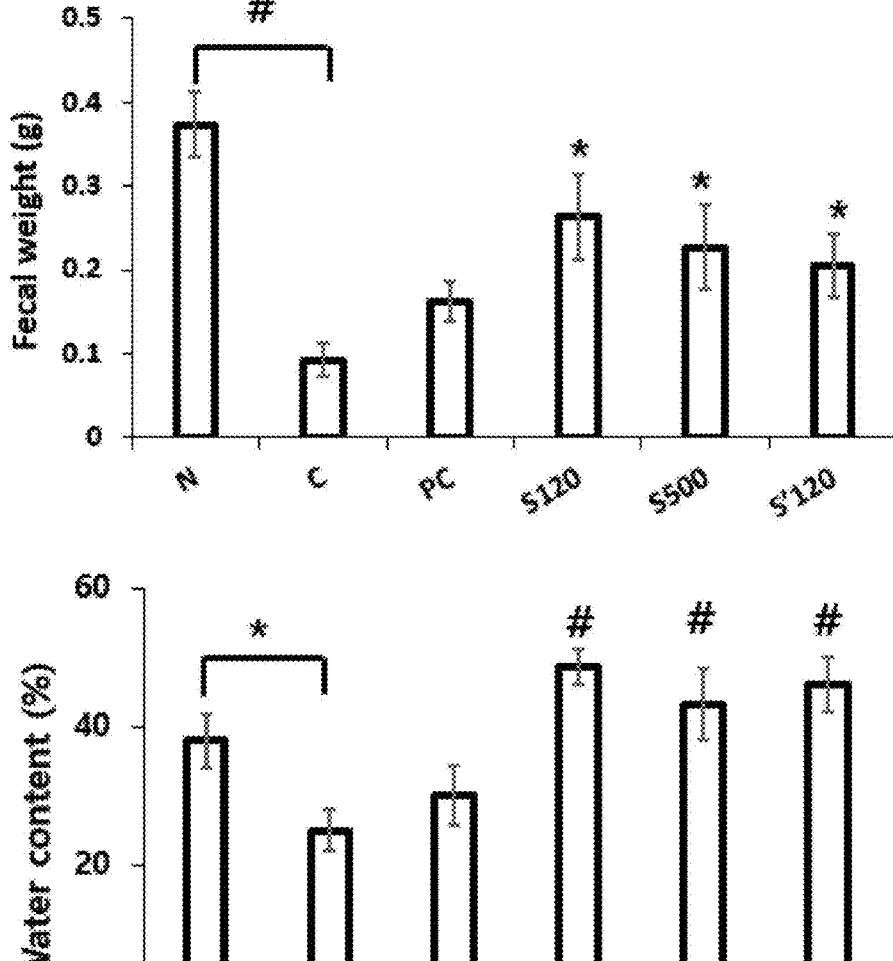

【Figure 2】
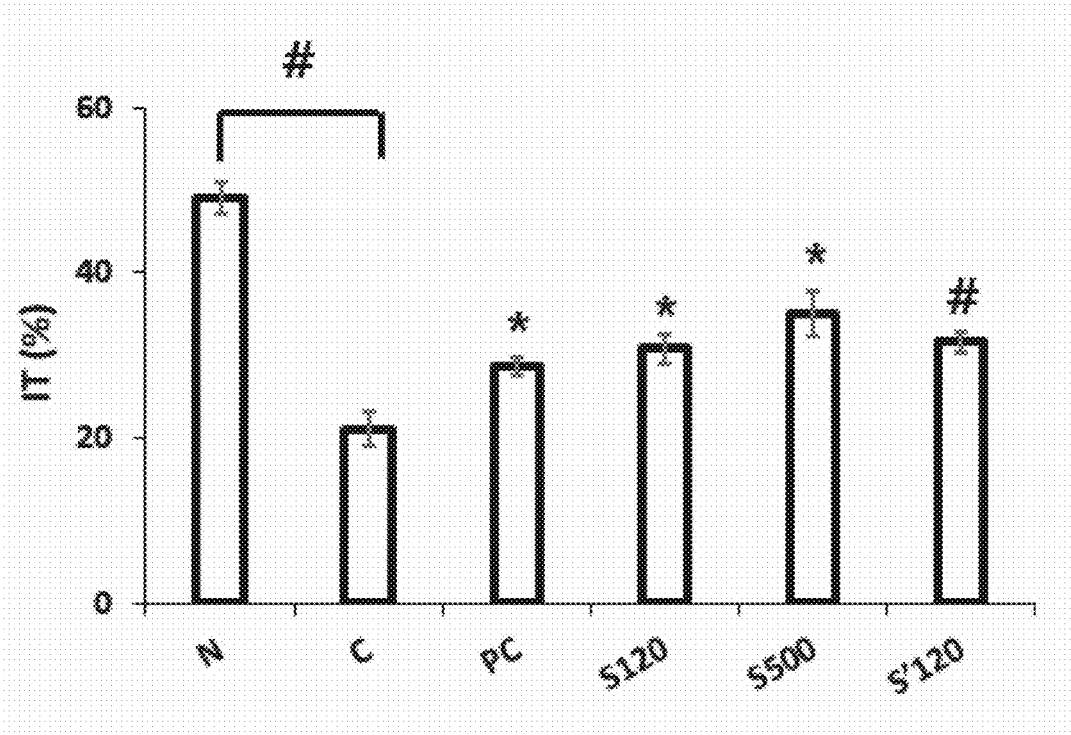
【Figure 3】
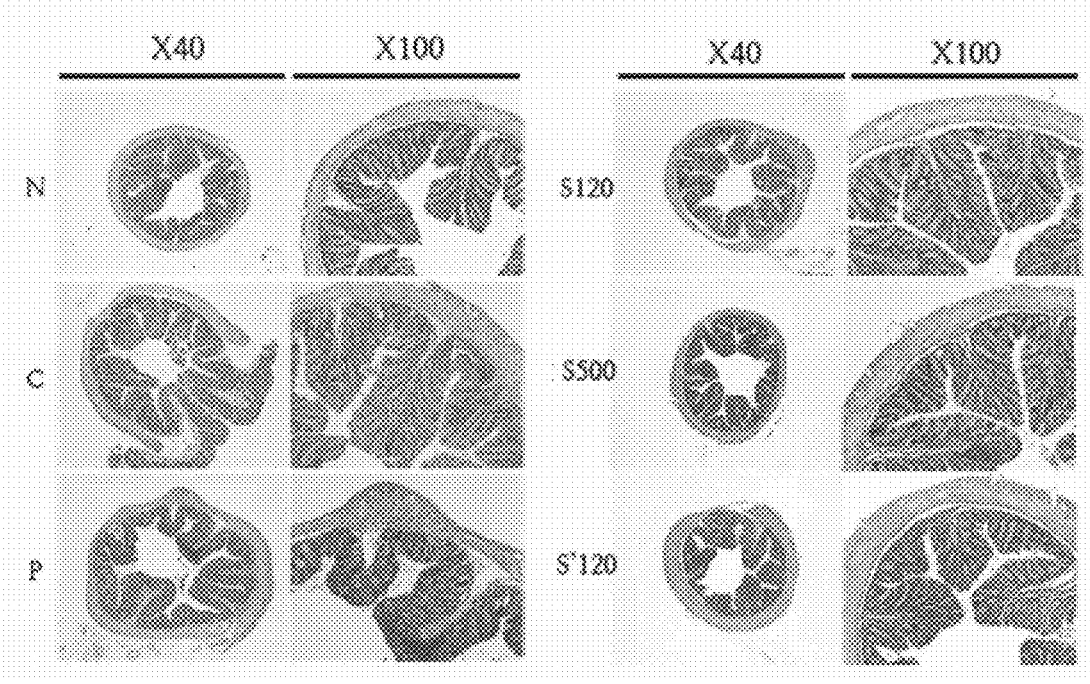

COMPOSITION COMPRISING CRICKET OR EXTRACT THEREOF FOR IMPROVING BOWEL MOVEMENT FUNCTION

This application is a National Stage Application of PCT/KR2021/005194, filed 23 Apr. 2021, which claims benefit of Patent Application Serial No. 10-2020-0049495, filed 23 Apr. 2020 in Korea and which applications are incorporated herein by reference. To the extent appropriate, a claim of priority is made to each of the above-disclosed applications.

TECHNICAL FIELD

The present invention relates to a composition comprising Cricket or an extract thereof for improving a bowel movement function or weight loss.

BACKGROUND ART

Bowel movement occurs through the relaxation and contraction (bowel movement reflex) of the intestines and muscles reflexively while the stimulation of the rectal mucosa by the intestinal contents transferred into the rectum is transmitted to the center to want to go to the toilet. However, when the bowel movement function is damaged according to autonomic dysfunction occurring in the lower digestive tract, excessive water absorption in the intestinal tract, decreased secretion of intestinal juice, movement disorders, gastrointestinal psychosomatic disease (e.g., irritable bowel syndrome), a decreased bowel movement reflex function, etc., large and small diseases or symptoms including constipation and abdominal obesity may be developed. To date, various medicines and functional foods for activating the bowel movement function and improving constipation or obesity have been sold, but there is a problem that the effect is temporary and various side effects are caused depending on a type.

Meanwhile, among edible insects proposed as future food, *Gryllus bimaculatus* is known to contain high-quality nutrient ingredients and is an insect registered as a food ingredient in Korea. Accordingly, there was an attempt to use the Cricket as a use for ingestion or a functional material In this regard, there are a study result of confirming an effect of preventing, improving or treating fatty liver disease of a *Gryllus bimaculatus* extract (Korean Patent Publication No. 2019-0003304), and a study result of confirming applicability of *Gryllus bimaculatus* as a functional material that promotes hair growth, prevents hair loss and improves hair follicles (Korean Patent Registration No. 1,702,851), but attempts to use Cricket in relation to improvement of the bowel movement function are insufficient. In particular, there is no result of directly studying the efficacy on how Cricket can help in preventing or improving constipation or obesity.

Under this background, the present inventors experimentally confirmed the efficacy of a Cricket extract for improving a bowel movement function and activating intestinal motility, and newly confirmed that the Cricket can be used for preventing, improving or treating constipation or obesity.

DISCLOSURE

Technical Problem

An object of the present invention is to provide a composition for improving a bowel movement function through an increase in fecal weight, an increase in water content in feces, an increase in gastrointestinal transport capacity, and an increase in length and area of a mucous membrane.

Another object of the present invention is to provide a method for improving a bowel movement function, comprising administering Cricket or an extract thereof to a subject.

Yet another object of the present invention is to provide Cricket or an extract thereof to be used for improving a bowel movement function.

Yet another object of the present invention is to provide the use of Cricket or an extract thereof to be used for preparing products, foods, or drugs for improving a bowel movement function.

Another object of the present invention is to provide a composition for improving constipation.

Yet another object of the present invention is to provide a method for preventing or improving constipation, comprising administering Cricket or an extract thereof to a subject.

Yet another object of the present invention is to provide Cricket or an extract thereof to be used for preventing or improving constipation.

Yet another object of the present invention is to provide the use of Cricket or an extract thereof to be used for preparing products, foods, or drugs for preventing or improving constipation.

Yet another object of the present invention is to provide a health functional food for improving constipation.

Yet another object of the present invention is to provide a method for preventing or improving constipation, comprising administering Cricket or an extract thereof to a subject.

Yet another object of the present invention is to provide Cricket or an extract thereof to be used for preventing or improving constipation.

Yet another object of the present invention is to provide the use of Cricket or an extract thereof to be used for preparing products, foods, or drugs for preventing or improving constipation.

Yet another object of the present invention is to provide a composition for weight loss.

Yet another object of the present invention is to provide a method for weight loss, comprising administering Cricket or an extract thereof to a subject or a subject having weight gain.

Yet another object of the present invention is to provide Cricket or an extract thereof to be used for weight loss.

Yet another object of the present invention is to provide the use of Cricket or an extract thereof to be used for preparing products, foods, or drugs for weight loss.

Yet another object of the present invention is to provide a health functional food for weight loss comprising Cricket or an extract thereof.

Technical Solution

To this end, an aspect of the present invention provides a composition for improving a bowel movement function, comprising Cricket or an extract thereof.

Another aspect of the present invention provides a method for improving a bowel movement function, comprising administering Cricket or an extract thereof to a subject.

Yet another aspect of the present invention provides Cricket or an extract thereof to be used for improving a bowel movement function.

Yet another aspect of the present invention provides the use of Cricket or an extract thereof to be used for preparing products, foods, or drugs for improving a bowel movement function.

Yet another aspect of the present invention provides a composition for improving constipation comprising Cricket or an extract thereof.

Yet another aspect of the present invention provides a method for preventing or improving constipation, comprising administering Cricket or an extract thereof to a subject.

Yet another aspect of the present invention provides Cricket or an extract thereof to be used for preventing or improving constipation.

Yet another aspect of the present invention provides the use of Cricket or an extract thereof to be used for preparing products, foods, or drugs for preventing or improving constipation.

Yet another aspect of the present invention provides a composition for improving constipation comprising Cricket or an extract thereof.

Yet another aspect of the present invention provides a composition for weight loss comprising Cricket or an extract thereof.

Yet another aspect of the present invention provides a method for weight loss comprising administering Cricket or an extract thereof to a subject or a subject having weight gain.

Yet another aspect of the present invention provides Cricket or an extract thereof to be used for weight loss.

Yet another aspect of the present invention provides the use of Cricket or an extract thereof to be used for preparing products, foods, or drugs for weight loss.

Yet another aspect of the present invention provides a health functional food for weight loss comprising Cricket or an extract thereof.

Hereinafter, the present application will be described in detail.

In an aspect, the present invention provides a composition for improving a bowel movement function, comprising Cricket or an extract thereof.

As used herein, the term 'improvement' refers to all actions including improvement, suppression, or delay of symptoms, and may be used interchangeably with prevention or treatment.

The prevention may be all actions of suppressing the corresponding disease or delaying the onset thereof by administering the composition to the subject, and the treatment may be all actions of improving the symptoms of the corresponding pre-infected disease by administering the composition to the subject.

As used herein, the term 'improvement of the bowel movement function' refers to all actions of maintaining a normal bowel movement condition or improving an abnormal bowel movement condition. For example, the improvement of the bowel movement function may include induction of bowel movement, facilitation of bowel movement, regular bowel movement of irregular bowel movement, an increase in water content included in feces, an increase in bowel movement, increased bowel movement, improved symptoms related to constipation or diarrhea, or prevention or improvement of weight loss or abdominal obesity, and may be used in combination with improving defecation or improving bowel movement. Specifically, the improvement of the bowel movement function may mean an increase in fecal weight, an increase in water content in feces, an increase in gastrointestinal transport capacity, or an increase in length and area of the intestinal mucosa.

The composition of the present invention includes Cricket or an extract thereof, and specifically, the Cricket or the extract thereof may be included as an active ingredient of the composition.

The 'Cricket' used in the composition of the present invention belongs to the family Gryllidae, Orthoptera, and includes subspecies and variants thereof. In addition, the Cricket of the present invention includes insects of the family Gryllidae that are apparent in the art and can be used for the same or similar purposes as the prevention, improvement and treatment of the present invention. Specifically, in the present specification, Cricket may be *Gryllus bimaculatus* recognized as a food raw material.

As used herein, the term 'extract' means isolating an active ingredient or specific ingredient thereof by dissolving a certain substance in a solvent, or isolating the active ingredient or specific ingredient thereof by treating a certain substance with an enzyme. Specifically, the extract includes an extract extracted by adding an extraction solvent to the Cricket, and a fraction fractionated by adding a fractional solvent to the extract. In addition, the extract includes an enzyme extract obtained by treating Cricket with an enzyme.

Specifically, a solvent extract of Cricket of the present invention may be an extract using water, an organic solvent, or a mixed solvent thereof.

The solvent may be at least one organic solvent selected from the group consisting of alcohols having 1 to 5 carbon atoms, acetone, acetonitrile, ethyl acetate, chloroform, dichloromethane, ethyl ether, xylene and hexane, water, or a mixture thereof. The alcohol having 1 to 5 carbon atoms may be alcohol having 1 to 4 carbon atoms, 1 to 3 carbon atoms, 2 to 5 carbon atoms, 2 to 4 carbon atoms, 2 to 3 carbon atoms, or 1 to 2 carbon atoms, for example, ethanol, but is not limited thereto. The ethanol may be edible ethanol, and when extraction is performed using the ethanol as a solvent, alcohol widely used commercially may be used.

In the present specification, the term 'enzyme extract' may be used in the same meaning as an 'enzyme analyte', 'enzyme hydrolysate', or 'enzyme-treated product'.

Specifically, the enzyme extract may be Cricket treated with protrease. For example, the content of amino acids or peptides may be increased by treating the protease in an aqueous supernatant obtained by centrifuging a crushed product of Cricket.

The protease may be any one or more selected from the group consisting of pepsin, trypsin, Flavourzyme™, Protamex™, papain, alpha chymotrypsin, and pancrease.

In the specification, the Cricket extract may be prepared by filtration, concentration and/or drying after extraction.

The filtration is to remove solid particles suspended from the extract to obtain only a water-soluble supernatant excluding a precipitate, and may use filtering particles using a filter such as cotton or nylon, for example, a filter having pores of 0.2 μm to 5 μm in diameter, a cryofiltration method, a centrifugation method, or the like, but is not limited thereto.

The concentration is to increase the concentration of the solid content of the extract, and a concentrate of the extract obtained through the concentration has a feature that is easier to be used as a food material. The concentration may be performed by vacuum concentration, plate-type concentration, thin film concentration, etc., but is not limited thereto, and for example, may be performed at a temperature of 40° C. to 60° C. using a known concentrator.

The brix of the present invention expresses the amount of solids contained in 100 g of a solution (water) as the number of grams based on saccharides (sugar), and may be used in combination with brix %, bx, and the like. The brix may be measured by a known method, and may be measured at room temperature such as 15° C. to 35° C.

The drying includes freeze drying, vacuum drying, hot air drying, spray drying, reduced pressure drying, spray drying, foam drying, high frequency drying, infrared drying, and the like, but is not limited thereto.

In the case of using the Cricket itself in the composition of the present invention, a crushed product or powder of Cricket may be included.

The Cricket crushed product (powder) may be crushed after fasting and drying the *Nemobius sylvestris*.

The composition of the present invention may be administered to mammals such as rats, mice, livestock, and humans by various routes. The 'administration' includes a method of delivering the composition to a system of the subject or a particular area in or on the subject. The administration may be performed, for example, enterally, parenterally, intravenously, intramuscularly, subcutaneously, intradermally, intranasally, orally, transdermally, endometrially, intracerebroventricularly or mucously. In addition, the composition may also be administered locally or systemically.

The composition may be administered together with one or more active ingredients exhibiting the same or similar function. For administration, according to a method that can be easily performed by a person of ordinary skill in the art to which the present invention pertains, one or more additionally acceptable carriers may be included. The meaning of 'acceptable' means that it does not inhibit the activity of the active ingredient and does not have more than adaptable toxicity of an application (prescription) target. The 'carrier' is defined as a compound that facilitates the addition of the compound into a cell or tissue. The composition may be formulated using a carrier and/or excipient to be prepared in a unit dose form or prepared by pouring into a multi-dose container, and may additionally include a dispersing agent or a stabilizing agent. In addition, the active ingredient included in the composition may be delivered in carriers, such as colloidal suspensions, powders, saline, lipids, liposomes, microspheres, or nano spherical particles. These active ingredients may form or be related to a complex with a vehicle and may be delivered in vivo by using delivery systems known in the art, such as lipids, liposomes, microparticles, gold, nanoparticles, polymers, condensation reagents, polysaccharides, polyamino acids, dendrimers, saponin, adsorption enhancing substances or fatty acids. Besides, the carrier may include lactose, dextrose, sucrose, sorbitol, mannitol, starch, acacia gum, calcium phosphate, alginate, gelatin, calcium silicate, microcrystalline cellulose, polyvinylpyrrolidone, cellulose, water, syrup, methylcellulose, methylhydroxybenzoate, propylhydroxybenzoate, talc, magnesium stearate, mineral oil, and the like, which are generally used in preparation, but is not limited thereto. Further, the carrier may further include a lubricant, a wetting agent, a sweetening agent, a flavoring agent, an emulsifying agent, a suspending agent, a preservative, and the like in addition to the above ingredients. The carrier may be used by mixing saline, sterile water, a Ringer's solution, buffered saline, a dextrose solution, a maltodextrin solution, glycerol, ethanol, and one or more of these components, and if necessary, other conventional additives such as antioxidants, buffers, bacteriostats, etc. may be added.

When the composition of the present invention is used for food, the active ingredient (Cricket extract) included in the composition may be added to food as it is or used with other foods or food ingredients, and may be appropriately used according to a conventional method. The composition may include other ingredients as essential ingredients without particular limitation, in addition to the active ingredients.

For example, like general beverages, various flavoring agents or natural carbohydrates may be included as an additional ingredient. Examples of the above-mentioned natural carbohydrates may include general sugars, such as monosaccharides, for example, glucose, fructose and the like; disaccharides, for example, maltose, sucrose and the like; and polysaccharides, for example, dextrin, cyclodextrin and the like, and sugar alcohols such as xylitol, sorbitol, erythritol, and the like. As flavoring agents other than those described above, natural flavoring agents (tauumatin, stevia extract (e.g., Rebaudioside A, glycyrginine, etc.)) and synthetic flavoring agents (saccharin, aspartame, etc.) may be advantageously used. The ratio of the natural carbohydrates may be appropriately determined by the selection of those skilled in the art. The composition may include various nutrients, vitamins, minerals (electrolytes), flavoring agents such as synthetic and natural flavoring agents, coloring agents, and enhancers (cheese, chocolate, etc.), pectic acid and salts thereof, alginic acid and salts thereof, organic acid, a protective colloidal thickener, a pH adjusting agent, a stabilizer, a preservative, glycerin, alcohol, a carbonic acid agent used in a carbonated drink, and the like. These ingredients may be used independently or in combination, and the ratio of these additives may also be appropriately selected by those skilled in the art.

When the composition of the present application is used pharmaceutically, the composition may be administered in various oral and parenteral formulations during actual clinical administration, and for formulations, the composition is formulated by using commonly used diluents or excipients, such as a filler, an extender, a binder, a wetting agent, a disintegrant, and a surfactant. Solid formulations for oral administration include a tablet, a pill, a powder, a granule, a capsule, and the like, and these solid formulations may be prepared by mixing at least one excipient, for example, starch, calcium carbonate, sucrose, lactose, gelatin, or the like with herbal extracts or herbal fermented products. Further, lubricants such as magnesium stearate talc may be used in addition to simple excipients. The powders may be prepared by simply mixing the active ingredient of the present invention with a suitable pharmaceutically acceptable carrier, such as lactose, starch, and microcrystalline cellulose. The granules may be prepared by mixing the active ingredient of the present invention, a suitable pharmaceutically acceptable carrier, and a suitable pharmaceutically acceptable binder such as polyvinylpyrrolidone and hydroxypropylcellulose, and then using a wet granulation method using a solvent such as water, ethanol, and isopropanol or a dry granulation method using a compressive force. Further, the tablets may be prepared by mixing the granules with a suitable pharmaceutically acceptable lubricant such as magnesium stearate, and then tableting the mixture using a tablet machine. Liquid formulations for oral administration may correspond to suspensions, oral liquids, emulsions, syrups, and the like, and may include various excipients, for example, a wetting agent, a sweetener, an aromatic agent, a preserving agent, and the like, in addition to water and liquid paraffin which are commonly used simple diluents. Formulations for parenteral administration include a sterile aqueous solution, a non-aqueous solution, a suspension, an emulsion, a lyophilizing agent, and a suppository. As the non-aqueous solution and the suspension, propylene glycol, polyethylene glycol, vegetable oil such as olive oil, injectable ester such as ethyl oleate, and the like may be used. As a base of the suppository, witepsol, macrogol, Tween 61, cacao butter, laurinum, glycerol, gelatin, and the like may be used.

The active ingredient (Cricket extract) may be administered with an oral agent, an injection (e.g., intramuscular injection, intraperitoneal injection, intravenous injection, infusion, subcutaneous injection, implant), an inhalant, a nasal injection, a vaginal agent, a rectal agent, a sublingual agent, a transdermal agent, a topical agent, or the like according to a disease to be prevented, improved or treated and a condition of a subject, but is not limited thereto. Depending on a route of administration, the active ingredient may be prepared into a suitable dosage unit formulation including a pharmaceutically acceptable carrier, an additive, and a vehicle, which are commonly used and non-toxic. During the administration, the amount range of the Cricket extract as the active ingredient varies depending on the weight, age, sex, and health condition of a patient, a diet, an administration time, an administration method, an excretion rate, a target site, and the severity of disease.

In addition, when the composition is used pharmaceutically, the composition may be administered in a pharmaceutically effective dose. In the present invention, the 'pharmaceutically effective dose' refers to a sufficient amount to treat the diseases at a reasonable benefit/risk ratio applicable to medical treatment. An effective dose level may be determined according to factors including the type and severity of disease of a patient, activity of a drug, sensitivity to a drug, a time of administration, a route of administration, an emission rate, duration of treatment, and simultaneously used drugs, and other factors well-known in the medical field. The effective dose is generally 0.01 mg to 5000 mg per day per 1 kg of the body weight of an administered subject, and may be administered once or several times a day at regular time intervals according to the judgment of a doctor or pharmacist, but is not limited thereto. The composition may be administered as an individual therapeutic agent, or administered in combination with a therapeutic agent for diseases caused by other contaminants or a therapeutic agent for improving skin aging, and may be administered simultaneously, separately, or sequentially with existing therapeutic agents, and may be administered singly or multiply. It is important to administer an amount capable of obtaining a maximum effect with a minimal amount without side effects by considering all the factors, which may be easily determined by those skilled in the art. Specifically, the effective dose of the composition may vary depending on the age, sex, condition, and weight of a patient, absorbance of an active ingredient in vivo, an inactivation rate, an excretion rate, a disease type, and drugs to be used in combination, and may be increased or decreased according to a route of administration, the severity of obesity, sex, weight, age, and the like and may vary depending on the severity of a treating condition. If necessary, for convenience, the total daily dose may be divided and administered several times during a day. For example, the daily dose may be about 0.0001 mg/kg to about 10 g/kg per day, for example, the amount of about 0.001 mg/kg to about 1 g/kg may be administered once a day. In addition, the administration period may be 1 day to 2 months, but the composition may be administered without limitation until the prevention or treatment effect of the disease is exhibited. In addition, according to the judgment of the doctor or pharmacist, the composition may be administered several times a day at regular time intervals, for example, separately administered 2 to 3 times a day.

As another aspect for achieving the object of the present invention, the present invention provides a method for improving a bowel movement function, comprising administering Cricket or an extract thereof to a subject.

As used herein, the term 'subject' may be a subject including a human, or may be a subject other than the human. In addition, the term 'subject' may be a subject in need of administration of Cricket of the present invention, an extract thereof, or a composition comprising the same. The subject in need of the administration may include a subject who has been diagnosed with a related disease, a subject who has developed a related symptom, and a subject who wants to be administered for preventing the development of a disease or symptom or improving health. For example, in the present invention, the subject in need of the administration is a subject who has constipation, a subject to prevent constipation, a subject to improve or prevent abdominal obesity due to constipation, a subject to improve an abnormal bowel movement condition, and a subject to maintain a normal bowel movement condition.

As an embodiment, the present invention provides a method for improving a bowel movement function comprising feeding the food composition or pharmaceutical composition for improving the bowel movement function to a subject or subject with reduced bowel movement.

The Cricket extract, the food composition and the pharmaceutical composition for improving the bowel movement function, and administration are the same as those described above.

As another aspect for achieving the object of the present invention, the present invention provides Cricket or an extract thereof to be used for improving a bowel movement function.

As another aspect for achieving the object of the present invention, the present invention provides the use of Cricket or an extract thereof to be used for preparing products, foods, or drugs for improving a bowel movement function.

In another aspect, the present invention provides a composition for improving constipation comprising Cricket or an extract thereof.

The contents related to the Cricket extract and the composition are the same as those described in relation to the 'composition for improving the bowel movement function', and hereinafter, only specific configurations of the composition for improving constipation will be described.

The Cricket extract may be used as a composition for improving constipation by increasing a fecal weight, increasing the water content in feces to soften the bowel movement, improving a gastrointestinal transport capacity, and increasing the length and area of the mucous membrane to improve intestinal motility.

As used herein, the 'constipation' may include constipation caused by various causes. Specifically, the constipation may be transient constipation, a major cause of overeating or stress, atonic constipation or colonic constipation caused by a decrease in abdominal muscle strength due to lack of exercise or overwork, habitual or rectal constipation caused by a decrease in motor function of the large intestine and the desire to defecate, and spastic constipation or organic constipation caused by interfering with the passage of feces due to too strong movement of the large intestine.

In addition, the constipation may include constipation caused by drugs. Drugs that may cause constipation may include a calcium channel blocker, an anticholinergic agent, an analgesic, an antidepressant, an antihistamine, an antispasmodic, an anticonvulsant, an aluminum-containing antacid, an iron preparation, and the like.

As an embodiment, the present invention provides a method for improving constipation, comprising administering Cricket or an extract thereof to a subject.

In another embodiment, the present invention provides a composition comprising Cricket or an extract thereof to be used for improving constipation.

The Cricket extract and the composition according to the present invention may have the characteristics as described above. The administration is the same as described in relation to the 'composition for improving the bowel movement function'. The subject may be a mammal, specifically a human.

In yet another aspect, the present invention provides a health functional food for improving constipation, comprising Cricket or an extract thereof.

The Cricket extract is the same as described in relation to the 'composition for improving the bowel movement function', and the description of the constipation is the same as described above, and hereinafter, only specific configurations of the health functional food for improving constipation will be described.

The health functional food is a food with high medical and health care effects processed to efficiently exhibit a bioregulatory function in addition to nutritional supply, and may obtain useful effects for health purposes, such as regulating nutrients or physiological effects on the structure and function of the human body. The health functional food may be prepared by a method commonly used in the technical field of the present invention, and may be prepared by adding raw materials and ingredients to be commonly added in the art. In addition, the formulations of the health functional food may be prepared in various forms without limitations as long as being formulations recognized as a health functional food. Unlike general medicines, there are advantages that there are no side effects that can occur during long-term use of drugs by using the food as a raw material and portability is excellent. Accordingly, for the prevention or improvement of constipation, before or after the stage at which the symptoms appear, the health functional food may be used simultaneously with or separately from drugs for treatment. The health functional food includes a health food having an active health maintenance or promotion effect compared to general foods, and a health supplement food for the purpose of health supplementation, and in some cases, the terms of health functional food, health food, and health supplement food may be used interchangeably.

In the health functional food, the active ingredient (Cricket extract) may be added to the food as it is or used with other foods or food ingredients, and may be appropriately used according to a general method. The mixing amount of the active ingredients may be suitably determined according to the purpose of use thereof (for prevention or improvement of constipation). The active ingredients may be included in various amounts in the health functional food as long as the active ingredients have an effect of preventing or improving constipation, and may be added in an amount of 15 parts by weight or less, 14 parts by weight or less, 13 parts by weight or less, 12 parts by weight or less, 11 parts by weight or less, or 10 parts by weight or less based on the total weight of the health functional food. However, in the case of long-term ingestion for the purpose of health and hygiene or health regulation, the amount may be equal to or lower than the above range. The health functional food may include other ingredients as essential ingredients without particular limitation, in addition to the active ingredient. For example, like general beverages, various flavoring agents or natural carbohydrates may be included as an additional ingredient. Examples of the above-mentioned natural carbohydrates may include general sugars, such as monosaccharides, for example, glucose, fructose and the like; disaccharides, for example, maltose, sucrose and the like; and polysaccharides, for example, dextrin, cyclodextrin and the like, and sugar alcohols such as xylitol, sorbitol, erythritol, and the like. As flavoring agents other than those described above, natural flavoring agents (tauumatin, stevia extract (e.g., Rebaudioside A, glycyrginine, etc.)) and synthetic flavoring agents (saccharin, aspartame, etc.) may be advantageously used. The ratio of the natural carbohydrates may be appropriately determined by the selection of those skilled in the art.

The health functional food may include various nutrients, vitamins, minerals (electrolytes), flavoring agents such as synthetic and natural flavoring agents, coloring agents and enhancers (cheese, chocolate, etc.), pectic acid and salts thereof, alginic acid and salts thereof, organic acid, a protective colloidal thickener, a pH adjusting agent, a stabilizer, a preservative, glycerin, alcohol, a carbonic acid agent used in a carbonated drink, and the like. These ingredients may be used independently or in combination, and the ratio of these additives may also be appropriately selected by those skilled in the art.

As another aspect for achieving the object of the present invention, the present invention provides a method for preventing or improving constipation, comprising administering Cricket or an extract thereof to a subject.

In one embodiment, the present application provides a method for preventing or improving constipation, comprising administering the composition for improving the bowel movement function to a subject.

In another embodiment, the present invention provides a method for preventing or improving constipation, comprising administering the composition for improving the bowel movement function to a subject who is expected to develop constipation symptoms or has symptoms of constipation.

The Cricket extract, the composition for improving the bowel movement function, the subject and administration are the same as those described above.

As another aspect for achieving the object of the present application, the present invention provides Cricket or an extract thereof to be used for preventing or improving constipation.

As another aspect for achieving the object of the present application, the present application provides the use of Cricket or an extract thereof to be used for preparing products, foods, or drugs for preventing or improving constipation.

In yet another aspect, the present invention provides a composition for weight loss comprising Cricket or an extract thereof.

The Cricket extract and the composition are the same as those described in relation to the 'composition for improving the bowel movement function', and hereinafter, only peculiar configurations of the composition for weight loss will be described.

The composition may be usefully used for weight loss by increasing a fecal weight, increasing the water content in feces, and promoting intestinal motility to improve the bowel movement function and promote the intestinal motility.

As used herein, the term 'weight loss' refers to all actions of maintaining a normal weight or improving an overweight condition, and may be used interchangeably with weight reduction or body fat reduction. Specifically, the weight loss may be weight loss according to the improvement of bowel movement or weight loss according to the improvement of constipation.

The composition of the present invention has anti-obesity activity and may improve obesity.

As used herein, the term 'obesity' refers to a type of disease in which remaining energy after consumption of taken energy is converted into triglycerides and accumulated mainly in adipocytes of the abdomen and adipose tissue, and refers to a complex syndrome that is caused by various causes, such as genetic, nutritional, environmental, and social factors.

In the present invention, the obesity may be obesity caused by constipation, specifically, abdominal obesity.

As another aspect for achieving the object of the present invention, the present invention provides a method for weight loss comprising administering the Cricket or the extract thereof; or the composition for weight loss to a subject or a subject having weight gain.

As another aspect for achieving the object of the present application, the present application provides a method for preventing or improving obesity comprising administering the Cricket or the extract thereof; or the composition for weight loss to a subject or a subject having obesity.

The Cricket extract, the composition for weight loss, the subject, and the administration are the same as those described above.

As another aspect for achieving the object of the present invention, the present invention provides Cricket or an extract thereof to be used for weight loss.

As another aspect for achieving the object of the present application, the present invention provides the use of Cricket or an extract thereof to be used for preparing products, foods, or drugs for weight loss.

The Cricket, the Cricket extract or the composition comprising the same according to the present invention may have the characteristics as described above. In addition, a group administered with the Cricket or the Cricket extract of the present invention may have no or low toxicity. In addition, the group administered with the Cricket or the Cricket extract of the present invention may have no or low possibility of side effects. Specifically, the group administered with the Cricket or the Cricket extract of the present invention may exhibit a change in weight gain similar to that of a normal control group, or have an organ weight similar to that of the normal control group.

Advantageous Effects

According to the present invention, the composition comprising the Cricket or the extract thereof has an excellent effect of improving a bowel movement function by increasing a fecal weight, increasing the water content in feces to soften bowel movement, and increasing the length and area of the mucous membrane to improve intestinal motility and thus may be usefully used for preventing, improving or treating constipation.

The effects of the present application are not limited to the effects mentioned above, and other effects not mentioned will be clearly understood by those skilled in the art from the following description.

DESCRIPTION OF DRAWINGS

FIG. 1 is a diagram illustrating the results of measuring fecal weight and water content in feces to determine an effect of administration of a Cricket extract on a fecal index. [N (Normal): normal control; C (Control): loperamide alone; PC (Positive control): *Psyllium* husk 120 mg/kg; S120: loperamide+Cricket enzyme extract 120 mg/kg; S500: loperamide+Cricket enzyme extract 500 mg/kg; S'120: loperamide+Cricket etanol extract 120 mg/kg, an error bar represents a standard error, and n=5].

FIG. 2 is a diagram illustrating the results of measuring digestive tract mobility to determine an effect of administration of a Cricket extract on a gastrointestinal transport capacity. [N (Normal): normal control; C (Control): loperamide alone; PC (Positive control): *Psyllium* husk 120 mg/kg; S120: loperamide+Cricket enzyme extract 120 mg/kg; S500: loperamide+Cricket enzyme extract 500 mg/kg; S'120: loperamide+Cricket ethanol extract 120 mg/kg, an error bar represents a standard error, and n=5].

FIG. 3 is a diagram illustrating the results of staining a colon tissue with hematoxylin-eosin to determine an effect of administration of a Cricket extract on intestinal digestive movement.

BEST MODE

Hereinafter, the present invention will be described in detail by Examples and Experimental Examples. However, these Examples and Experimental Examples specifically illustrate the present invention, and the scope of the present invention is not limited to these Examples and Experimental Examples.

Preparation Example 1

Preparation of Cricket Enzyme Extract (1) Step of Fasting *Gryllus bimaculatus*

40 to 45-day-old *Gryllus bimaculatus* dieted on wheat grains was subjected to a process of excreting an excrement while fasting before use. The *Gryllus bimaculatus* after 24-hour fasting was washed and frozen-stored.

(2) Step of Hydrolyzing, Sterilizing, and Wet-Crashing *Gryllus bimaculatus*

100 parts by weight of the pretreated raw material was added with 1900 parts by weight of water and then sterilized at 100° C. for 30 minutes. Thereafter, the *Gryllus bimaculatus* was crushed with a homogenizer at 6000 rpm for 10 minutes to obtain a liquid form that was easily treated with enzymes.

(3) Step of Treating *Gryllus bimaculatus* Solution with Protease to Decompose Protein The crushed *Gryllus bimaculatus* solution was added with 0.1% of protease, Protamex, and treated at a temperature of 60° C. for 1 hour and then the enzyme was inactivated at 100° C. for 10 minutes.

(4) Step of Filtering *Gryllus bimaculatus* Extract

The protease-treated product was filtered under reduced pressure passing through 1 μm glass fiber filter paper, and then only a filtrate was taken.

(5) Step of Concentrating *Gryllus bimaculatus* Extract

The filtrate was concentrated with a vacuum concentrator to prepare a concentrate of 10 brix or more.

(6) Step of Powdering *Gryllus bimaculatus* Extract

The concentrate was lyophilized and powdered, and specifically, sequentially maintained at −45° C. for 6 hours, at −20° C. for 21 hours, at −15° C. for 11 hours, and at −5° C. for 11 hours and then thawed, and then powdered by removing moisture.

Preparation Example 2

Preparation of Cricket Ethanol Extract (1) Step of Fasting Cricket 40 to 45-day-old *Gryllus bimaculatus* dieted on wheat grains excreted an excrement while fasting for 24 hours and then was washed and frozen-stored.

(2) Step of Drying and then Crushing *Gryllus bimaculatus*

The frozen-stored *Gryllus bimaculatus* was washed and then dried at 90° C. for 24 hours. The dried raw material was finely crushed with a crusher for easy extraction.

(3) Step of Extracting *Gryllus bimaculatus* Powder by Adding Ethanol 100 parts by weight of the pretreated raw material was added with 900 parts by weight of ethanol and then extracted at 25° C. and 100 rpm for 24 hours.

(4) Step of Filtering *Gryllus bimaculatus* Extract

The extract was filtered under reduced pressure through 1 µm glass fiber filter paper, and then only a filtrate was taken.

(5) Step of Concentrating *Gryllus bimaculatus* Extract

The filtrate was concentrated with a vacuum concentrator to prepare a concentrate of 10 brix or more.

(6) Step of Powdering *Gryllus bimaculatus* Extract

The concentrate was lyophilized and powdered, and specifically, sequentially maintained at −45° C. for 6 hours, at −20° C. for 21 hours, at −15° C. for 11 hours, and at −5° C. for 11 hours and then thawed, and then powdered by removing moisture.

EXPERIMENTAL EXAMPLE

Confirmation of Bowel Movement Function of Cricket Extract

Experimental Example 1. Breeding of Experimental Animals and Design of Experiments This study was conducted in accordance with the policies and regulations of the Institutional Animal Care and Use committee (SEMI-19-008) of Southeast Medi-Chem Institute. As experimental animals used in the experiment, a 7-week-old ICR mouse model (male) was received from Hana Bio (Seongnam, Gyeonggi-do, Korea) and quarantined, acclimatized and bred in an animal kennel (Animal Facility Registration Certificate: No. 412) and then experimented. During breeding, a lighting time was set to a 12-hour (07:00 to 19:00) cycle, and a diet and water were freely ingested.

First, 5 ICR mice (7 weeks old, male) were placed in each group, and the experimental groups were classified into a total of 6 groups. The experimental groups were divided into a normal control group (N), a loperamide administered group (C), a *Psyllium* husk administered group (PC), a loperamide+low concentration Cricket enzyme extract administered group (120 mg/kg) (S120), a loperamide+high concentration Cricket enzyme extract administered group (500 mg/kg) (S500), and a loperamide+low concentration Cricket ethanol extract administered group (120 mg/kg) (S'120).

The samples were orally administered for a total of 7 days according to the contents in Table 1, and on day 7 of administration, all the groups except for the normal control group were orally administered with 5 mg/kg of loperamide (in saline) to induce constipation. For a feed, solid feed for the experimental animals (Hana Bio, Seongnam, Gyeonggi-do, Korea) was provided, and changes in body weight was measured twice a week.

TABLE 1

| Group | Experiment | Note |
|---|---|---|
| Control group 1 (N) | Administration of saline | No administration of Loperamide |
| Control group 2 (N) | Saline | |
| Control group 3 (PC) | Psyllium husk 120 mg/kg | |
| Example 1 (S120) | Preparation Example 1 120 mg/kg | |
| Example 2 (S500) | Preparation Example 1 500 mg/kg | |
| Example 3 (S'120) | Preparation Example 2 120 mg/kg | |

The measured experimental results were represented as means and standard errors, and the significance test of each group was statistically processed using an anova t-test in the Statview program.

Experimental Example 2. Confirmation of Changes in Fecal Index by Cricket Extract The feces of the experimental animals were collected after administration of loperamide (5 mg/kg, body weight) on day 6 of sample administration, and the weight and number of feces per subject were measured. In order to check the water content in feces, a change amount was calculated by comparing a weight immediately after collection with a weight after drying at 105° C. for 48 hours.

Water content (%)=[(weight before drying−weight after drying)/weight before drying]×100

The results were shown in Table 2 and FIG. 1.

TABLE 2

| Group | The number of subjects | After administration of loperamide Fecal weight (g) | After administration of loperamide Water content (%) |
|---|---|---|---|
| Control group 1 (N) | 5 | 0.373# | 37.99* |
| Control group 2 (N) | 5 | 0.093 | 25.01 |
| Control group 3 (PC) | 5 | 0.163 | 30.03 |
| Example 1 (S120) | 5 | 0.263* | 48.61# |
| Example 2 (S500) | 5 | 0.227* | 43.12* |
| Example 3 (S'120) | 5 | 0.205* | 46.10# |

1) Table 2 shows the experimental results as means and standard errors. Significance was represented for each group as follows: * compared with P<0.05 C group, #compared with P<0.001 C group.

N (Normal): normal control; C (Control): loperamide alone administered group; PC (Positive control): *Psyllium* husk 120 mg/kg; S120: loperamide+Cricket enzyme extract 120 mg/kg; S500: loperamide+Cricket enzyme extract 500 mg/kg; S'120: loperamide+Cricket ethanol extract 120 mg/kg As shown in Table 2 and FIG. 1, the fecal weight showed a significant decrease in group C causing constipation, compared to group N without causing constipation, but in groups S120 and S500 administered with the Cricket enzyme extract, the fecal weight was increased as compared to group C, and larger than that in group PC administered with *Psyllium* husk.

In addition, the water content in feces showed a significant decrease in group C causing constipation, compared to group N without causing constipation, but in all of groups S120, S500, and S'120 administered with the Cricket extract, the water content in feces was significantly high as compared with group C, and higher than that of the normal control group.

As a result, it was confirmed that the Cricket extract prevented the decrease in fecal weight and improved the bowel movement function by increasing the water content in feces, so that it was confirmed that an effect of preventing or improving constipation was excellent.

Experimental Example 3. Confirmation of Changes in Digestive Tract Mobility Rate by Cricket Extract In order to observe an effect of a Cricket extract on a gastrointestinal transport capacity, the digestive tract mobility rate was evaluated. The digestive tract mobility rate may be evaluated by measuring the length of movement of an administered indicator material out of the entire length of the small intestine at a certain time, and in this experiment, loperamide, which exhibited a gastrointestinal transport inhibition effect, was used as a drug for causing constipation, and phenol red was used as an indicator material.

Specifically, 5 mg/kg of loperamide was orally administered after 1 hour of the administration of the Cricket extract. After 30 minutes of loperamide administration, 0.5% phenol red (in 1.5% methylcellulose) serving as an indicator was orally administered, and autopsy was performed after 20 minutes to measure the total intestinal length and a movement distance of phenol red. The measurement results were analyzed using the following equation, which was calculated as a percentage of the movement distance of phenol red with respect to the total intestinal length. The analysis results were shown in Table 3 and FIG. 2.

Digestive tract mobility rate (%)=(movement distance of Phenol red/total intestinal length)×100

TABLE 3

| Group | The number or subjects | Digestive tract mobility rate (%) |
|---|---|---|
| Control group 1 (N) | 5 | 49.0$^{\#}$ |
| Control group 2 (N) | 5 | 21.1 |
| Control group 3 (PC) | 5 | 28.8* |
| Example 1 (S120) | 5 | 30.8* |
| Example 2 (S500) | 5 | 35.0$^{\#}$ |
| Example 3 (S'120) | 5 | 31.7* |

1) Table 3 shows the experimental results as means and standard errors. Significance was represented for each group as follows: * compared with P<0.05 C group, #compared with P<0.001 C group.
2) N (Normal): normal control; C (Control): loperamide alone administered group; PC (Positive control): *Psyllium* husk 120 mg/kg administered group; S120: loperamide+Cricket enzyme extract 120 mg/kg; S500: loperamide+Cricket enzyme extract 500 mg/kg; S'120: loperamide+Cricket ethanol extract 120 mg/kg As shown in Table 3 and FIG. 2, the digestive tract mobility rate was significantly reduced in group C causing constipation, compared to group N, whereas it was confirmed that in the Cricket extract administered group, the digestive tract mobility rate was significantly increased compared to group C (p<0.05, p<0.001). Furthermore, it was shown that in the Cricket extract administered group, the digestive tract mobility rate was higher than that of group PC administered with the *Psyllium* husk extract.

From this, it was confirmed that the Cricket extract activated the digestive movement of the intestine, and as a result, it was confirmed that the Cricket extract can be effectively applied to the prevention or improvement of constipation.

Experimental Example 4. Confirmation of Structural Changes in Colon Tissue by Cricket Extract To determine an effect of the Cricket extract on the colon tissue, the colon tissue was stained with Hematoxylin & Eosin (H&E).

Specifically, the colon tissue extracted from each experimental group was immobilized in 4% paraformaldehyde immediately after extraction, washed with water, dehydrated, transparent, and penetrated, and then embedded with paraffin.

The prepared paraffin block was micro-sectioned and sliced, and then stained with H&E staining. The stained slides were photographed after observation with an optical microscope (Nikon, E600, Japan), and the results were shown in FIG. 3.

As illustrated in FIG. 3, it was observed that the length and area of the mucous membrane were significantly reduced in group C causing constipation, compared to non-treated group N, and it was confirmed that in the Cricket extract administered group, the length and area of the mucous membrane were increased compared to group C.

From this, it was confirmed that the Cricket extract could help the digestive movement of the intestine, and as a result, it was confirmed that the Cricket extract can be effectively applied to the prevention or improvement of constipation.

Considering the above results, the Cricket extract showed significant increases in fecal weight, water content in feces, digestive tract mobility rate, and length and area of the mucous membrane compared to a loperamide-administered control group, so that the very excellent effect of improving the bowel movement function and improving intestinal motility was exhibited. Meanwhile, clear dose dependence was observed in 120 and 500 mg/kg administered groups, and the Cricket enzyme extract 120 mg/kg administered group helped the absorption of water in the intestine at the level equivalent to or higher than that of *Psyllium* husk set as a positive control, so that the effective dose of the Cricket extract was determined around 120 mg/kg.

The invention claimed is:

1. A method of improving a bowel movement function in a subject in need thereof, comprising:
   administering an effective amount of a composition comprising cricket extract to the subject in need thereof,
   wherein the cricket extract is an enzyme extract, and
   wherein the administering results in improved bowel movement function in the subject in need thereof.

2. The method of claim 1, wherein the enzyme extract is prepared by decomposing a protein by protease.

3. The method of claim 1, wherein the improvement of the bowel movement function is an increase in fecal weight, an increase in water content in feces, an increase in gastrointestinal transport capacity, or an increase in length and area of intestinal mucosa.

4. A method of improving constipation in a subject in need thereof, comprising:
   administering an effective amount of a cricket extract to the subject in need thereof,
   wherein the cricket extract is an enzyme extract, and
   wherein the administering results in improved constipation in the subject in need thereof.

5. The method of claim 4, wherein the constipation is transient constipation, atonic constipation, spastic constipation, bowel movement impaired constipation, or organic constipation.

* * * * *

18